Figure 2:
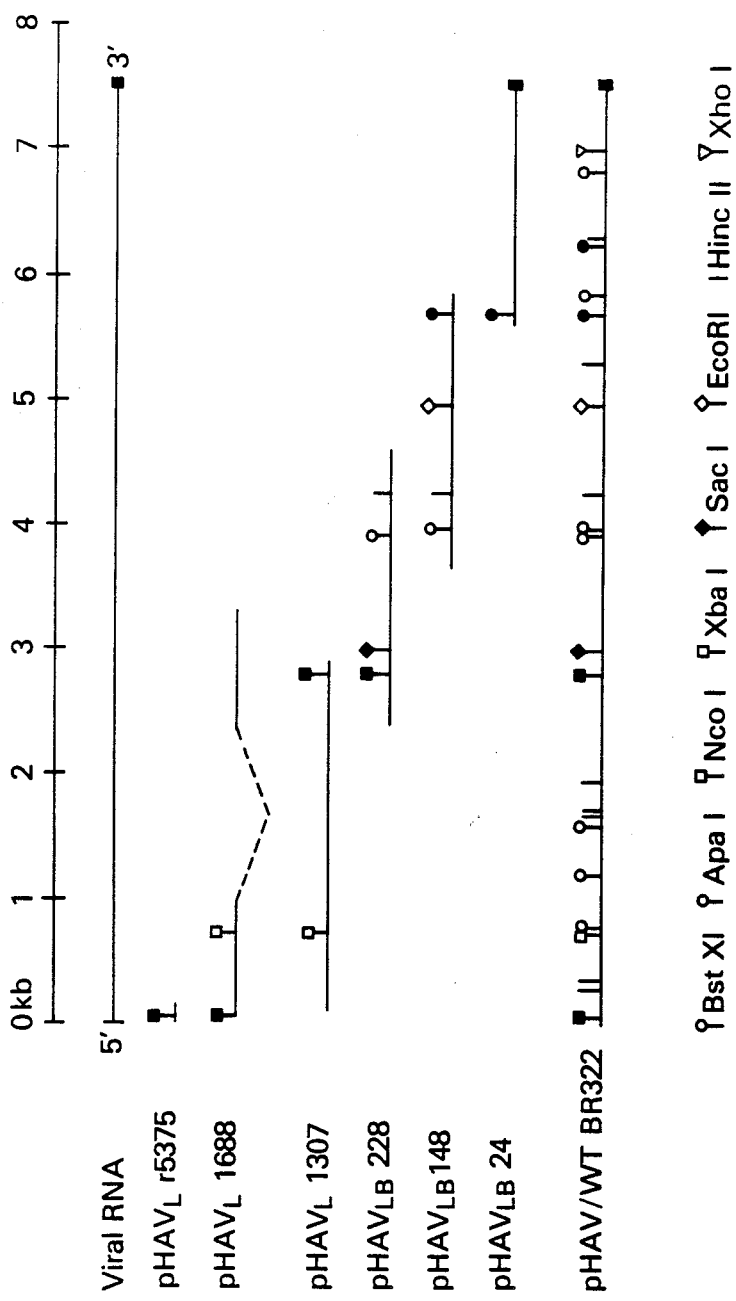

United States Patent [19]

Purcell et al.

[11] Patent Number: 4,894,228

[45] Date of Patent: Jan. 16, 1990

[54] VACCINE AGAINST HEPATITIS A VIRUS

[75] Inventors: Robert H. Purcell, Boyds; John R. Ticehurst, Kensington, both of Md.; Jeffrey I. Cohen, Newton, Mass.; Suzanne U. Emerson, Silver Spring, Md.; Stephen M. Feinstone; Richard J. Daemer, both of Washington, D.C.; Ian D. Gust, Melbourne, Australia

[73] Assignee: The United States of America as represented by the Department of Health and Human Services, Washington, D.C.

[21] Appl. No.: 217,824

[22] Filed: Jul. 12, 1988

Related U.S. Application Data

[63] Continuation-in-part of Ser. No. 905,146, Sep. 9, 1986, abandoned, which is a continuation-in-part of Ser. No. 652,067, Sep. 19, 1984, Pat. No. 4,620,978.

[51] Int. Cl.$^4$ ............................................. A61K 39/29
[52] U.S. Cl. ...................................... 424/89; 514/894
[58] Field of Search ........................... 424/89; 514/894

[56] References Cited

U.S. PATENT DOCUMENTS 4,164,566  8/1979  Provost et al. ........................ 424/89
4,620,978 11/1986  Daemer et al. ...................... 435/237

OTHER PUBLICATIONS

Feinstone, S. M., Daemer, R. J., Gust, I. D., Purcell, R. H., Live Attenuated Vaccine for Hepatitis A, Dev. Biol. Stand., 1983; 54: 429–432.

Provost, P. J., Conti, P. A., Giesa, P. A. et al., Studies in Chimpanzees of Live, Attenuated Hepatitis A Vaccine Candidates, Proc. Soc. Exp. Biol. Med., 1983; 172: 357–363.

Ticehurst, J. R., Racaniello, V. R., Baroudy, B. M., Baltimore, D., Purcell, R. H., Feinstone, S. M., Molecular Cloning and Characterization of Hepatitis A Virus cDNA, Proc. Natl. Acad. Sci. USA, 1983; 80: 5885–5889.

von der Helm, K., Winnacker, E. L., Deinhardt, F. et al., Cloning of Hepatitis A Virus Genome, J. Virol. Methods, 1981; 3: 37–43.

Daemer et al., Infection and Immunity, 32(1): 388–393, Apr. 1981.

Purcell et al., "Hepatitis A Virus" (in press).

Primary Examiner—Ronald W. Griffin
Attorney, Agent, or Firm—Mishrilal Jain

[57] ABSTRACT

The present invention provides an attenuated hepatitis A virus useful as a vaccine.

6 Claims, 12 Drawing Sheets

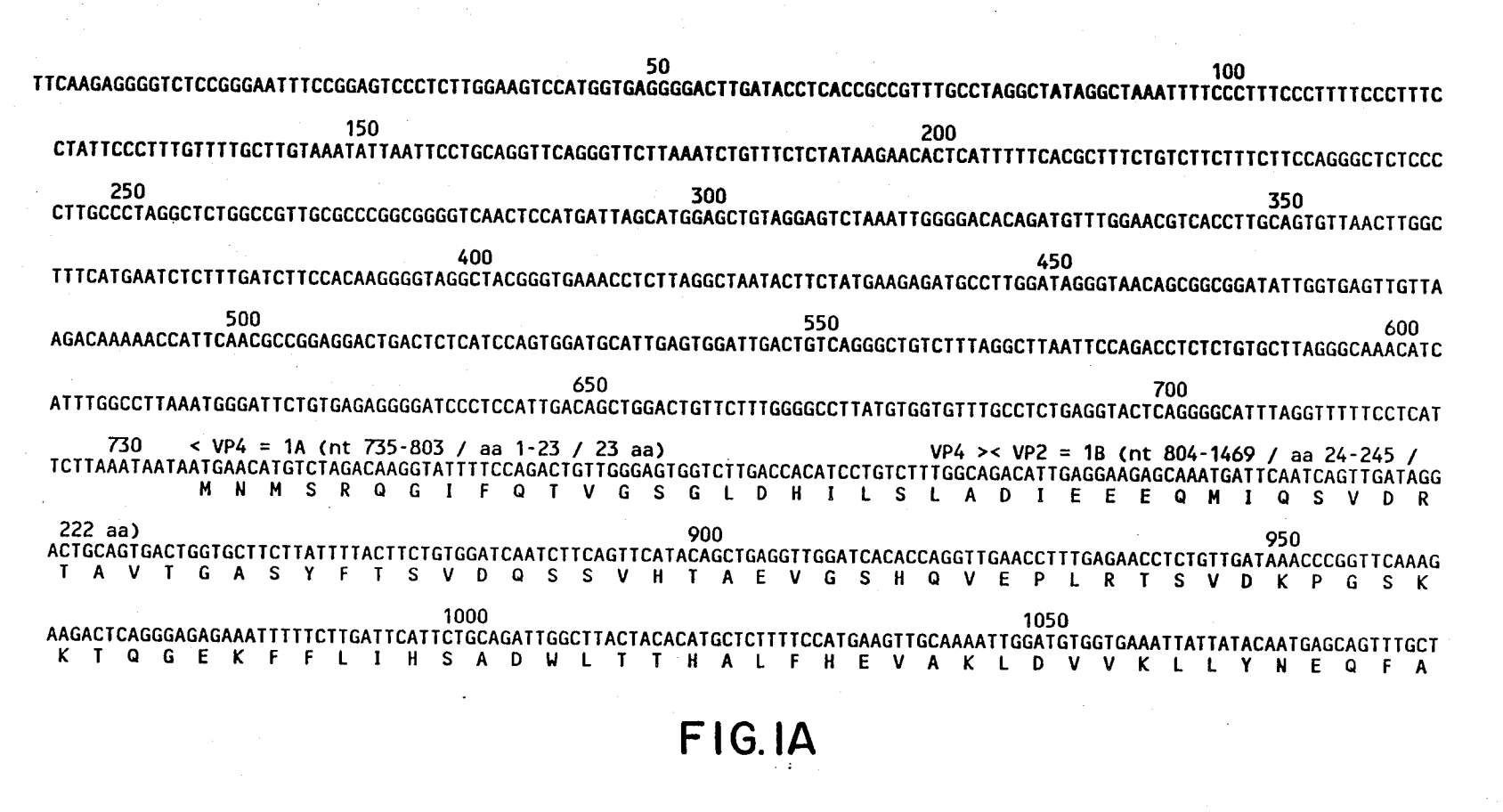

FIG. IA

```
                                                          1150                                                                                            1200
GTTCAAGGGTTGTTGAGATACCATACATATGCAAGATTTGGCATTGAAATTCAAGTTCAGATAAACCCTACACCTTTCCAACAGGGGGGATTGATCTGTGTGCTATGGTTCCTGGTGACCAG
 V  Q  G  L  L  R  Y  H  T  Y  A  R  F  G  I  E  I  Q  V  Q  I  N  P  T  P  F  Q  Q  G  G  L  I  C  A  M  V  P  G  D  Q
                                             1250                                                 1300
AGCTATGGTTCTATAGCATCATTGACTGTTTATCCTCATGGTTTGTTAAATTGCAATATTAACAATGTGGTTAGAATAAAGGTTCCATTTATTACACAAGAGGTGCTTACCACTTTAAA
 S  Y  G  S  I  A  S  L  T  V  Y  P  H  G  L  L  N  C  N  I  N  N  V  V  R  I  K  V  P  F  I  Y  T  R  G  A  Y  H  F  K
                                         1350                                                 1400
GATCCACAATACCCAGTTTGGGAATTGACAATTAGAGTTTGGTCAGAATTAAATATTGGACAGGAACTTCAGTTATACTTCACTCAATGTTTAGCTTATGATTTGGAGTTG
 D  P  Q  Y  P  V  W  E  L  T  I  R  V  W  S  E  L  N  I  G  T  S  A  Y  T  S  L  N  V  L  A  R  F  T  D  L  E  L
         1450           VP2 >< VP3 = 1C (nt 1470-2207 / aa 246-491 / 246 aa)                               1550
CATGGATTAACTCCCTCTTTCTACACAAATGATGAGAAATGAATTTAGGGTCAGTACTACTGAGAATGTGAATCTGTCAAATATGAAGATGCAAGAGCAAAGATGTCTTTTGCTTTG
 H  G  L  T  P  L  S  T  Q  M  M  R  N  E  F  R  V  S  T  T  E  N  V  V  N  L  S  N  Y  E  D  A  R  A  K  M  S  F  A  L
                                                     1650
GATCAGGAAGATTGGAAATCTGATCCGTCCCAGGGTGGTGGGATCAAAATTACTCATTTCTTGACATCTATTCCAACTTTGGCTGCTCCAGTTCCATTTAATGCTTCAGACTCA
 D  Q  E  D  W  K  S  D  P  S  Q  G  G  G  I  K  I  T  H  F  T  T  W  T  S  I  P  T  L  A  A  Q  F  P  F  N  A  S  D  S
                                             1700                                                 1750                                                 1800
GTTGGTCAACAAATTAAAGTTATTCCAGTTGACCCATATTTTTTCCAAATGACAAATCCTGACCAAAAATGTATAACTGCTTTGGCTCTATTTGTCAGATGTTTGTTTTGG
 V  G  Q  Q  I  K  V  I  P  V  D  P  Y  F  F  Q  M  T  N  P  D  Q  K  C  I  T  A  L  A  S  I  C  Q  M  F  C  F  W
                                                                         1850                                                 1900
AGAGGAGATCTTGTCTTTGATTTCAAGTTTTCCACCAAATATCATTCAGGTAGATTACTGTTTTGTTCCTGGCAATGAGCTAATAGATGTTTCTGGAATCACATTAAAGCAA
 R  G  D  L  V  F  D  F  Q  V  F  P  T  K  Y  H  S  G  R  L  L  F  C  F  V  P  G  N  E  L  I  D  V  S  G  I  T  L  K  Q
```

FIG.1B

```
                                                                        2000
GCAACTACTGCTCCTTGTGCAGTAATGGATATTACAGGAGTGCAGTCAACTTTGAGATTTGTGTTCCCTGGATTTCTGACACTTCTACAGAGTGAACAGGTATACAAAGTCAGCACAT
 A  T  T  A  P  C  A  V  M  D  I  T  G  V  Q  S  T  L  R  F  V  P  W  I  S  D  T  P  Y  R  V  N  R  Y  T  K  S  A  H
   2050                                                                                       2150
CAGAAAGGTGAGTACACTGCCATTGGGAAGCTTATTGTGTATTGTTATAACAGATTGACCTCTCCTTCAACGTTGCTTCCCATGTCAGAGTGAATGTTATCTTTCAGCAATTAACTTG
 Q  K  G  E  Y  T  A  I  G  K  L  I  V  Y  C  Y  N  R  L  T  S  P  S  N  V  A  S  H  V  R  V  N  V  Y  L  S  A  I  N  L

GAATGTTTTGCTCCTCTTTATCATGCTATGGATGTTACTACACAAGTTGGAGATGATTCTGGAGGTTTTTCAACAGTTTCTACAGAACAGATGTTCCAGATCCCCAAGTTGGTATA
 E  C  F  A  P  L  Y  H  A  M  D  V  T  T  Q  V  G  D  D  S  G  G  F  S  T  T  V  S  T  E  Q  N  V  P  D  P  Q  V  G  I
         2200 VP3 >< VP1 = 1D (nt 2208-3107 / aa 492-791 / 300 aa)                                                  2400
ACAACCATGAAAGATTTGAAAGGAAAAGCTAACAGAGGAAAATGTATGGATGTTTCAGGAGTACATCACAAGCACCTGTGGGAGCTATCACAACAATTGAGGATCCAGTTTTAGCAAAGAAAGTACCT
 T  T  M  K  D  L  K  G  K  A  N  R  G  K  M  D  V  S  G  V  Q  A  P  V  G  A  I  T  T  I  E  D  P  V  L  A  K  K  V  P
                                       2450                                              2500
GAGACACATTTCTGAATTGAAACCTGGAGAATCCAGACATACATCAGATCATATGTCCATTACAAGTTTATGGGAAGGTCTCATTTCTGTGCACTTTTACATTCAATTCAATAATAAA
 E  T  F  P  E  L  K  P  G  E  S  R  H  T  S  D  H  M  S  I  Y  K  F  M  G  R  S  H  F  L  C  T  F  F  T  F  N  S  N  N  K
     2550                                                                            2600
GAGTACACATTCCCTATAACCCTGTCTCTCAACCTCTAATCCTCAACCTCTCCATGGTTTGCCATCAACAACTGAGGTGGTTTTTCAACTTGTTTCAGTTGTATAGAGGGCCTTTAGATCTGACAATT
 E  Y  T  F  P  I  T  L  S  S  T  S  N  P  P  H  G  L  P  S  T  L  R  W  F  F  N  L  F  Q  L  Y  R  G  P  L  D  L  T  I
         2650                                                              2700                                 2750
ATTATTACAGGAGCAACTGATGTAGATGGCATGGCCTGGTTCACTCCAGTAGGTCTTGCCGTTGATACTCCTTGGGTAGAGAAGGAGTCAGCTTTGTCTATTGACTACAAAACTGCTCTT
 I  I  T  G  A  T  D  V  D  G  M  A  W  F  T  P  V  G  L  A  V  D  T  P  W  V  E  K  E  S  A  L  S  I  D  Y  K  T  A  L

FIG.IC
```

```
GGAGCTGTCAGATTTAACACAAGGAGAACAGGAACATTCAGATTAGATTACCATGGTATTCTTATTTATATGCTGTGTCTGGAGCACTGGATGGTTTGGGTGACAAGACAGATTCTACA
 G  A  V  R  F  N  T  R  R  T  G  N  I  Q  I  R  L  P  W  Y  S  Y  L  Y  A  V  S  G  A  L  D  G  L  G  D  K  T  D  S  T
                             2800                                  2850                                              3000
TTTGGATTGGTTTCTATTCAGATTGCAAATTACAATCATTCTGATGAATACTTGTCTTTTAGTTGTCTATTTGTCTGTCAGTACAATCAGAGTTTATTTTCCCAGAGCTCCATTGAAC
 F  G  L  V  S  I  Q  I  A  N  Y  N  H  S  D  E  Y  L  S  F  S  C  Y  L  S  V  T  E  Q  S  E  F  Y  F  P  R  A  P  L  N
                   2900                                  2950                           3050                3100 VP1 >< 2A
TCAAATGCCATGTTATCCACTGAATCAATGATGAGCAGAATTGCAGCTGGAGACTTGGAGTCATCAGTGGATGATCCTAGACAGGAGAATAAAGATTTGAGAGTCATATAGAATGC
 S  N  A  M  L  S  T  E  S  M  M  S  R  I  A  A  G  D  L  E  S  S  V  D  D  P  R  S  E  E  D  K  R  F  E  S  H  I  E  C
(nt 3108-3674 / aa 792-980 / 189 aa)
AGGAAGCCATATAAAGAACTGAGATTAGAAGTTGGGAAACAAAGACTCAAGTATGCTCAGGAAGAATTGTCAAATGAAGTACTTCCACCCCCTAGGAAAATGAAGGACTGTTTTCACAA
 R  K  P  Y  K  E  L  R  L  E  V  G  K  Q  R  L  K  Y  A  Q  E  E  L  S  N  E  V  L  P  P  P  R  K  M  K  G  L  F  S  Q
                                  3200                                  3250                             3300           3350
GCCAAAATTTCTCTTTTTTATACTGAGGAGCATGAAATAATGAAGTTTCCTGGAGAGGTTTAAGGAGTTTGGATTCTCTTTGGCCGCAGGCAGAAGT
 A  K  I  S  L  F  Y  T  E  E  H  E  I  M  K  F  S  W  R  G  V  T  A  D  T  R  A  L  R  R  F  G  F  S  L  A  A  G  R  S
                                              3400                                                      3450
GTGTGGACTCTTGAAATGGATGCTGGGGTTCTTACTGGGGAGACTGATTAGATTAGATGAAGATGACAAGATTGTTTCATTGATTGAAAAGTTTACAAGT
 V  W  T  L  E  M  D  A  G  V  L  T  G  R  L  I  R  L  N  D  E  K  W  T  E  M  K  D  D  K  I  V  S  L  I  E  K  F  T  S
                         3500                                  3550                                              3600
AACAAATATTGGTCAAAGTGAATTTCCCAACATGGAATCTTGAAGAAATTGCTGCCAATTCTAAGGATTTTCCTAACATGTCTGAAACGGATTTGTGTTTTCTGCTGCATTGG
 N  K  Y  W  S  K  V  N  F  P  H  G  M  L  D  L  E  E  I  A  A  N  S  K  D  F  P  N  M  S  E  T  D  L  C  F  L  L  H  W
```

```
     4450
AGCTTAACATCAATTGGCAACCAAATTTGTAAACATTATGGTGTTGAGCCTGAAAAGAATATCTATACTAAACCTGTGGCTTCAGATTACTGGGATGGATATAGTGGACAATTA
 S   L   T   S   I   A   L   A   T   K   I   C   K   H   Y   G   V   E   P   E   K   N   I   Y   T   K   P   V   A   S   D   Y   W   D   G   Y   S   G   Q   L
                                                                4500                                                                                  4550
GTTTGCATCATTGATGATATTGGCCAAAACACAACAGATGAGGATTGGTCAGATTTTTGTCAGGATGTCAGGAGATGTCCAATGAGATTAAACATGGCCTCTCTTGAGGAGAAGGGTAGG
 V   C   I   I   D   D   I   G   Q   N   T   T   D   E   D   W   S   D   F   C   Q   L   V   S   G   C   P   M   R   L   N   M   A   S   L   E   E   K   G   R
                   4600                                                                  4650
CATTTTCTCTCCTTTTATAATAGCAACTTCAAATTGGTCAAATCCAAGTTTATGTTAAGGAAGCAATTGACCGACTCCATTTCAAGGTTGAAGTAAACCTGCT
 H   F   S   S   P   F   I   I   A   T   S   N   W   S   N   P   S   P   •   K   T   V   Y   V   K   E   A   I   D   R   R   L   H   F   K   V   E   V   K   P   A
         4700                                                                4750                                                                4800
TCATTTTTCAAAAATCCTCACAATGATATGTTGAATGTTAATTAGCTAAACAAATGATGCAATCAAAGATATGTCTTGTTGATTTGATAATGTTTCATTGATG
 S   F   F   K   N   P   H   N   D   M   L   N   V   N   L   A   K   T   N   D   A   I   K   D   M   S   C   V   D   L   I   M   D   G   H   N   V   S   L   M
                                 4850                                                                  4900
                                                                                                          2C >< 3A (nt 5001-5222 / aa 1423-1496 / 74 aa)
GATTTGCTCAGTTCTTAGTCATGACAGTTGAAATTAGAAAACAAATGACTGAATTCATGGAGTTGTGGTCTCAGGAATTCAGATGATAATGTCAGTAGCTGAGTTT
 D   L   L   S   S   L   V   M   T   V   E   I   R   K   Q   N   M   T   E   F   M   E   L   W   S   Q   G   I   S   D   D   D   N   D   S   A   V   A   E   F
             4950                                                                                5000
TTCCAGTCTTTTCCATCTGGTGAACCATCGAACTCTAAATTATCTGGCTTTTCCAATCTGTTACTAATCACAAGTGGGTTGCTGTGGGAGCTCAGTTGGCATTCTTGGAGTGCTGTT
 F   Q   S   F   P   S   G   E   P   S   N   S   K   L   S   G   F   F   Q   S   V   T   N   H   K   W   V   A   V   G   A   A   V   G   I   L   G   V   L   V
                         5100                                                                                5150
                                                 3A >< 3B = VPg (nt 5223-5291 / aa 1497-1519 / 23 aa)
GGAGGATGGTTTGTGTATAAGCATTTCTCCCGCAAAGAGGAGGAACCAATCCCAGCTGAAGGGTATATCATGGTGTAACTAAGCCAAGCAAGTGATTAAATTAGATGCAGATCCAGTA
 G   G   W   F   V   Y   K   H   F   S   R   K   E   E   E   P   I   P   A   E   G   V   Y   H   G   V   T   K   P   K   Q   V   I   K   L   D   A   D   P   V
                             5200                                                                                    5250
```

FIG.1G

```
                                                                                 6200
TTACCTATTGTAGAAGAACCAGAGATTATAAAGAGGCTTCAATTTTTATCAAAATAAATAGTGGGTAAGACTCAGTTAGTTGATGATTTTTAGATCTTGATATGGCCATTACAGGG
 L  P  I  V  E  E  P  E  D  Y  K  E  A  S  I  F  Y  Q  N  K  I  V  G  K  T  Q  L  V  D  D  F  L  D  L  D  M  A  I  T  G
        6250                                                                                  6350
GCCCCAGGAATTGATGCTATCAACATGGATTCATCTCCTGGATTTCCTTATGTCCAGGAGAAGTTGACCAAAAGAGATTTAATTTGGTTGGATGAAAATGGTTTATTGCTGGGAGTTCAT
 A  P  G  I  D  A  I  N  M  D  S  S  P  G  F  P  Y  V  Q  E  K  L  T  K  R  D  L  I  W  L  D  E  N  G  L  L  G  V  H
                                         6450
CCAAGATTGGCTCAGAGAATCTTATTCAATACTGTCATGATGGAAAATTGTTCTGATTGGATGTGTTTTACAACCTGTCCAAAAGATGAATTGAGACCATTAGAGAAAGTGTTGGAA
 P  R  L  A  Q  R  I  L  F  N  T  V  M  M  E  N  C  S  D  L  D  V  V  F  T  T  C  P  K  D  E  L  R  P  L  E  K  V  L  E
                   6500                                                                                          6600
TCAAAAACAAGGACTATTGATGCTGTCCCTCTGGATTACTCAATTCTTTGTGCCGAATGTATTGGGGTCCAGTCTATTAGTAGTTTCATTTGAATCCAGGTTTCCATACAGGTGTTGCTATT
 S  K  T  R  A  I  D  A  C  P  L  D  Y  S  I  L  C  R  M  Y  W  G  P  A  I  S  Y  F  H  L  N  P  G  F  H  T  G  V  A  I
                                                          6700
GGCATAGATCCTGATAGACAGTGGGATGAATTATTTAAAACAATGATAAGATTCGGAGATGTTGGTCTTGATCTAGATTTCTCGCTTTGATGCTAGTCTTAGTCATTATGATTAGA
 G  I  D  P  D  R  Q  W  D  E  L  F  K  T  M  I  R  F  G  D  V  G  L  D  L  D  F  S  A  F  D  A  S  L  S  P  F  M  I  R
                                 6800
GAAGCAGGTAGAATCATGAGTGAACTATCTGGAACTCCATCCCATTTTGGCACAGCTCTTATCAATACTATCATTATTTATTCCAAGCATTTGTCTGTATAACTGTTGTTACCATGTCTGTGGT
 E  A  G  R  I  M  S  E  L  S  G  T  P  S  H  F  G  T  A  L  I  N  T  I  I  Y  S  K  H  L  L  Y  N  C  C  Y  H  V  C  G
         6850                                                                                6950
TCAATGCCCTCTGGGTCTCCTTGTACAGCTTTGCTAAATTCAATTATTAATAATGTCAATTATTATATGTGTTTTCCAAGATATTTGGAAAGTCTCCAGTTTTCTTTTGTCAGGCTTTG
 S  M  P  S  G  S  P  C  T  A  L  L  N  S  I  I  N  N  V  N  L  Y  Y  V  F  S  K  I  F  G  K  S  P  V  F  F  C  Q  A  L
```

FIG.1H

```
AAGATTCTCTGTTATGGAGATGATGTTTAATAGTTTTCTCTCGAGATGTTCAGATTGATAATCTTGATTTGATTGGACAAAAAATTGTAGATGAGTTTAAGAAACTTGGCATGACAGCT
 K  I  L  C  Y  G  D  D  V  L  I  V  F  S  R  D  V  Q  I  D  N  L  D  L  I  G  Q  K  I  V  D  E  F  K  K  L  G  M  T  A
                          7100                                  7150                                                              7200
ACTTCTGCTGACAAGAATGTACCTCAGCTGAAACCAGTTTCGGAATTGACTTTTCTCAAAAGATCTTCAATTGGTAGAGGATAGAATTAGACCTGCAATTTCGGAAAAAACAATTTGG
 T  S  A  D  K  N  V  P  Q  L  K  P  V  S  E  L  T  F  F  L  K  R  S  F  N  L  V  E  D  R  I  R  P  A  I  S  E  K  T  I  W
                          7250                                                              7300
TCTTTAATAGCATGGCAGAGAAGTAACGCTGAGTTTGAGCAGAATTTAGAAAATGCTCAGTGGTTTGCTTTTATGCATGGCTATGAGTTTTATCAGAAATTTATTATTTGTTCAGTCC
 S  L  I  A  W  Q  R  S  N  A  E  F  E  Q  N  L  E  N  A  Q  W  F  A  F  M  H  G  Y  E  F  Y  Q  K  F  Y  Y  F  V  Q  S
                 7350                                                                    3D > 7400
TGTTTGGAGAAAGAGATGATAGAATACAGACTTAAATCTTATGATTGGTGGAGAATGAGATTTTATGACCAGTGTTTCATTTGTGACCTTTCATGATTGTTAAACAAATTTCTTAAA
 C  L  E  K  E  M  I  E  Y  R  L  K  S  Y  D  W  W  R  M  R  F  Y  D  Q  C  F  I  C  D  L  S  *
 7450                                                             7478
ATTTCTGAGGTTTGTTTATTTCTTTTATCAGTAAATAAAAAAAAAAAAAAA
```

7000

7050

FIG.11

VACCINE AGAINST HEPATITIS A VIRUS

This application is a continuation-in-part of the application Ser. No. 905146 filed Sept. 9, 1986, now abandoned, which in turn is a continuation-in-part of Ser. No. 652,067 filed Sept. 19, 1984, now U.S. Pat. No. 4,620,978, issued Nov. 4, 1986.

SUMMARY OF THE INVENTION

The present invention provides complete nucleotide sequence of attenuated hepatitis A virus, HAV strain HM-175 Pass 35, which is significantly different from wild-type HAV. This new strain of HAV differs from wild-type HAV HM-175 by several nucleotide changes distributed throughout the genome, is attenuated for chimpanzees, elicits serum neutralizing antibodies, and is suitable for use as an HAV vaccine. It is noted, however, that not all the changes in HM-175 Pass 35 are necessary for attenuation and use as a vaccine. The attenuated virus of the present invention grows well in cell culture. the invention describes those mutations that are involved in cell culture adaptation and attenuation.

BACKGROUND OF THE INVENTION

Hepatitis A virus (HAV) is responsible for over 20,000 cases of hepatitis in the United States each year. Certain populations are at high risk for infection with HAV including foreign travelers, children attending day care centers and their close contacts, military personnel, and persons with close contact of patients with hepatitis A. Currently, passive immunization with immune serum globulin (ISG) is the only effective measure for preventing HAV infections in these patients. ISG, however, elicits only low levels of neutralizing antibody and requires repeated doses.

An effective vaccine would be useful for active immunization of populations at high risk. Inactivated HAV vaccines have been developed which are immunogenic and protective against challenge with the live virus [see Binn et al., *J. Infect. Dis.*, 153: 749–756 (1986) and Provost et al., *Proc. Soc. Exp. Biol. Med.*, 159: 201–203 (1978)]. These vaccines may prove effective; however, they are usually costly, may fail to produce local (or secretory) immunity, and may require repeated administration. Live HAV vaccines are under development—Provost et al. have shown that a cell culture adapted variant of HAV, strain CR-326, is attenuated (infectious, but no longer causes disease) in nonhuman primates and induces protection against challenge with wild-type (naturally occurring) virus. The experiments which constitute the parent applications of this invention disclose the development of a cell culture adapted variant of HAV, strain HM-175, which is attenuated and which elicits serum neutralizing antibody providing protection against challenge with wild-type virus in chimpanzees.

Wild-type HAV, strain HM-175, grows poorly in cell culture; however, after several passages the virus adapts to cell culture and becomes attenuated for chimpanzees [see Feinstone et al, *Develop. Biol. Standard,* 54: 429–432 (1983)]. The biological basis for cell culture adaptation and attenuation of HAV is unknown. The complete nucleotide sequence of the genome of wild-type (naturally occurring) HAV, strain HM-175, has been disclosed in Cohen et al., "Complete nucleotide sequence of wild-type hepatitis A virus: comparison with different strains of hepatitis A virus and other picornaviruses." Comparison of the nucleotide sequence between wild-type HAV HM-175 and attenuated HM-175/7 indicates that a maximum of 25 nucleotide changes (resulting in 12 amino acid changes) are responsible for cell culture adaptation and attenuation of HAV-175.

While the biological basis for attenuation is unknown, three areas of the HAV genome may contain markers of attenuation. The RNAs of the 5' non-coding regions of wild-type HAV and HM-175/7 have different predicted secondary structures. The 5' non-coding region of HAV HM-175 Pass 35 has five nucleotide deletions (one 4-base and one single-base deletion) when compared to wild-type HM-175. The 5' non-coding region has the highest degree of nucleotide conservation among the different strains of HAV. However, when wild-type HM-175 and HM-175/7 are compared, 28% of the nucleotide differences (7/25 bases) are present in the 5' noncoding region, a region which contains less than 10% of the viral genome. Thus, this relatively small area of the genome may be important for both cell culture adaptation and attenuation.

The capsid region of the HAV genome may also be important for attenuation. HAV HM-175 Pass 35 has two amino acid differences from wild-type HM-175 in the capsid region. The nucleotide difference at position 3025 changes amino acid 273 of VP1 from glutamic acid (negatively charged) in wild-type HM-175 to valine (non-polar) in HM-175/7. Thus, one of the amino acid differences between wild-type and attenuated HAV HM-175 may occur at a site important for antibody binding.

The nucleotide sequences of other strains of HAV have been disclosed. A partial sequence of a variant of HAV HM-175 propagated in a cell culture not suitable for vaccine use is disclosed in Ross et al., "Molecular cloning of cDNA from hepatitis A virus strain HM-175 after multiple passages in vivo and in vitro," *J. Gen. Virol.* This strain was derived from wild-type virus after multiple passages (6 in vivo and 59 in vitro) and virus released into cell culture medium was used for molecular cloning. A different cell culture adapted strain of HAV (not known to be attenuated and not acceptable for vaccine production) is disclosed in Najarian et al., *PNAS USA,* 82: 627–631 (1985). Like HAV HM-175 Pass 35, the Ross et al variant contains a deletion of a single thymine at the nucleotide position 203–207. However, the Ross et al variant contains seven other nucleotide differences from wild-type HAV HM-175 in the 5' coding region which the variant of the present invention does not. The Najarian et al. strain has numerous differences from wild-type HAV HM-175 including an adenine at position 203 and a thymine at the 3' end of the genome. This strain, like the strain of the present invention, also contains a nucleotide difference at position 6522, resulting in an amino acid change from wild-type HAV HM-175 of a serine to a threonine. All of the cell culture adapted HAV stains that have been sequenced in the capsid region have nucleotide differences from wild-type HAV HM-175 at positions 1742 and 2864 that do not result in amino acid changes from the wild-type.

SPECIFIC DISCLOSURE OF THE INVENTION

The present invention is the development of a variant of wild-type HAV HM-175—a variant which is attenuated in primates and useful as a vaccine. The nucleotide sequence of this variant are also disclosed (see Table 1). The mutations found in the P2 and P3 regions of the genome, excluding mutations at nucleotide positions at 7032 and 7430, have been shown to include the mutations that confer the attenuation characteristics on the HM-175 strain of HAV. Two nucleotide substitutions resulting in amino acid changes in the HAV protein 2B are quite important for growth in cell culture. In particular, the present invention provides the following:

1. An attenuated hepatitis A virus comprising a genome characterized by the following nucleotides: cytosine at positions 3919, 4043, 4222 and 4810; guanine at positions 964 and 3196; adenine at positions 1742, 2864, 4185, 4563, 5204, 6147 and 6522; and thymine at positions 3025, 3889, 4087 and 5232.

2. An attenuated hepatitis A virus comprising a genome coding for the following amino acids: an arginine is encoded at nucleotide position 964; valine at nucleotide positions 3196, 4222 and 4810; alanine at position 3919; methionine at position 4087; lysine at position 4185; isoleucine at position 4563; tyrosine at position 5232; asparagine at position 6147; and threonine at position 6522.

3. A tissue culture adapted hepatitis A virus comprising a genome characterized by a cytosine at nucleotide position 3919 and a thymine at nucleotide position 3889.

4. A tissue culture adapted hepatitis A virus comprising a genome coding for the following amino acids: an alanine at nucleotide position 3919 and a valine at nucleotide position 3889.

5. A pharmaceutical composition, comprising immunogenic amount of the virus of item 4 above and pharmaceutically acceptable carrier (such as non-toxic, sterile buffer, physiological saline and the like).

6. A method for inducing protective immunity against HAV, comprising administering to a host susceptible to HAV infection, immunogenic amount of the composition of item 5 above, to render said host immune to HAV infection.

Analysis of the nucleotide sequences of wild-type HAV HM-175 and attenuated HM-175/7 indicates that a maximum of 25 nucleotide changes (with 12 amino acid changes) are responsible for cell culture adaptation and attenuation of HAV HM-175. HAV HM-175/7 is different from all other known strains of hepatitis A virus in that it is attenuated in primates, grown in a cell culture, biologically and medically suitable for use as a vaccine.

The clone of the present invention may also contain a cytosine at nucleotide position 4810 (resulting in a serine), a cytosine at 7422 (non-coding), and a thymine at 7479 (non-coding).

HAV HM-175/7 is derived from HM-175/Clone 7, which represents the thirtieth passage of HM-175 in African green monkey kidney cells. HM-175/Clone 7, the master seed, is deposited in the American Type Culture Collection.

Figure 1E:
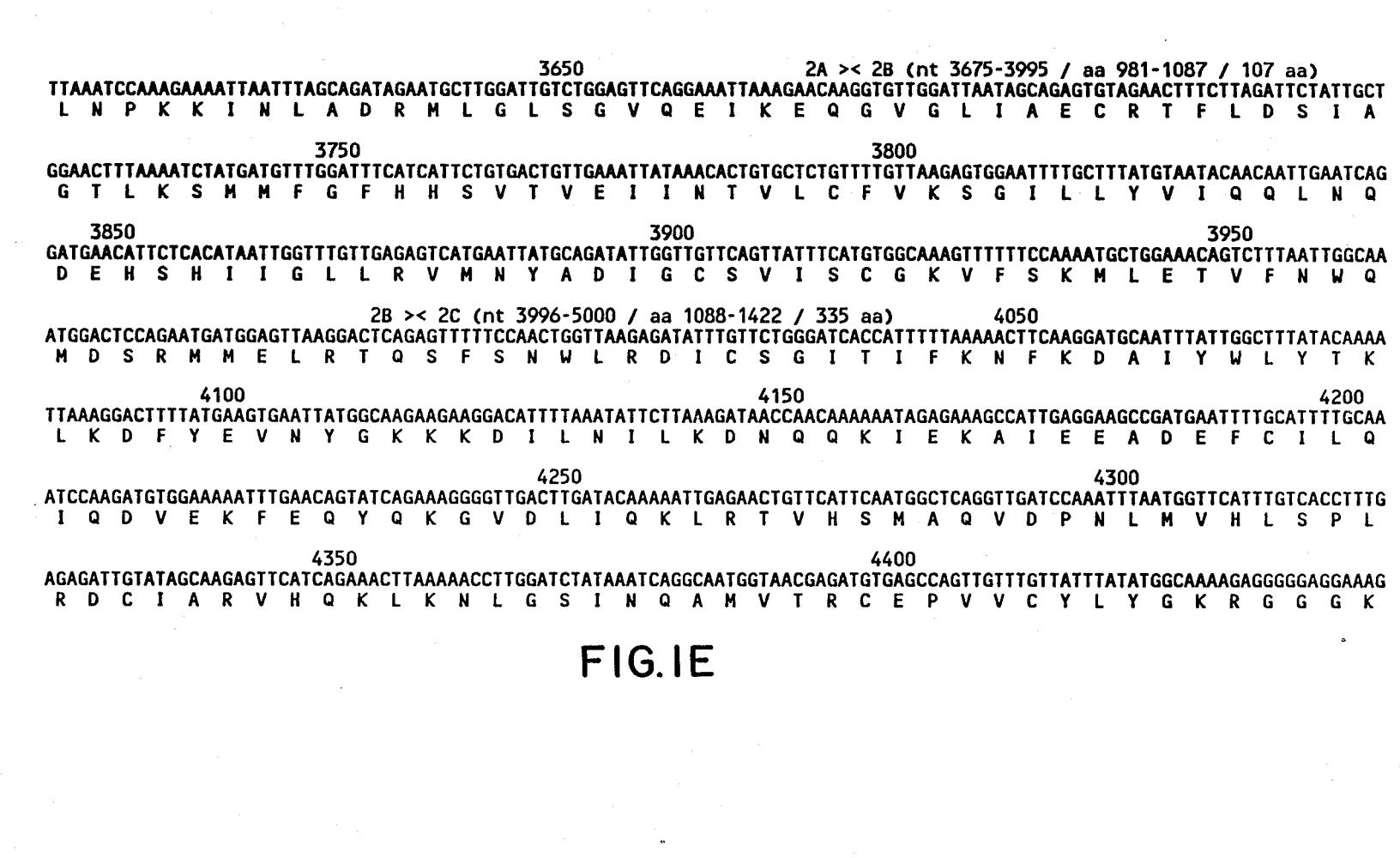
Figure 1G:
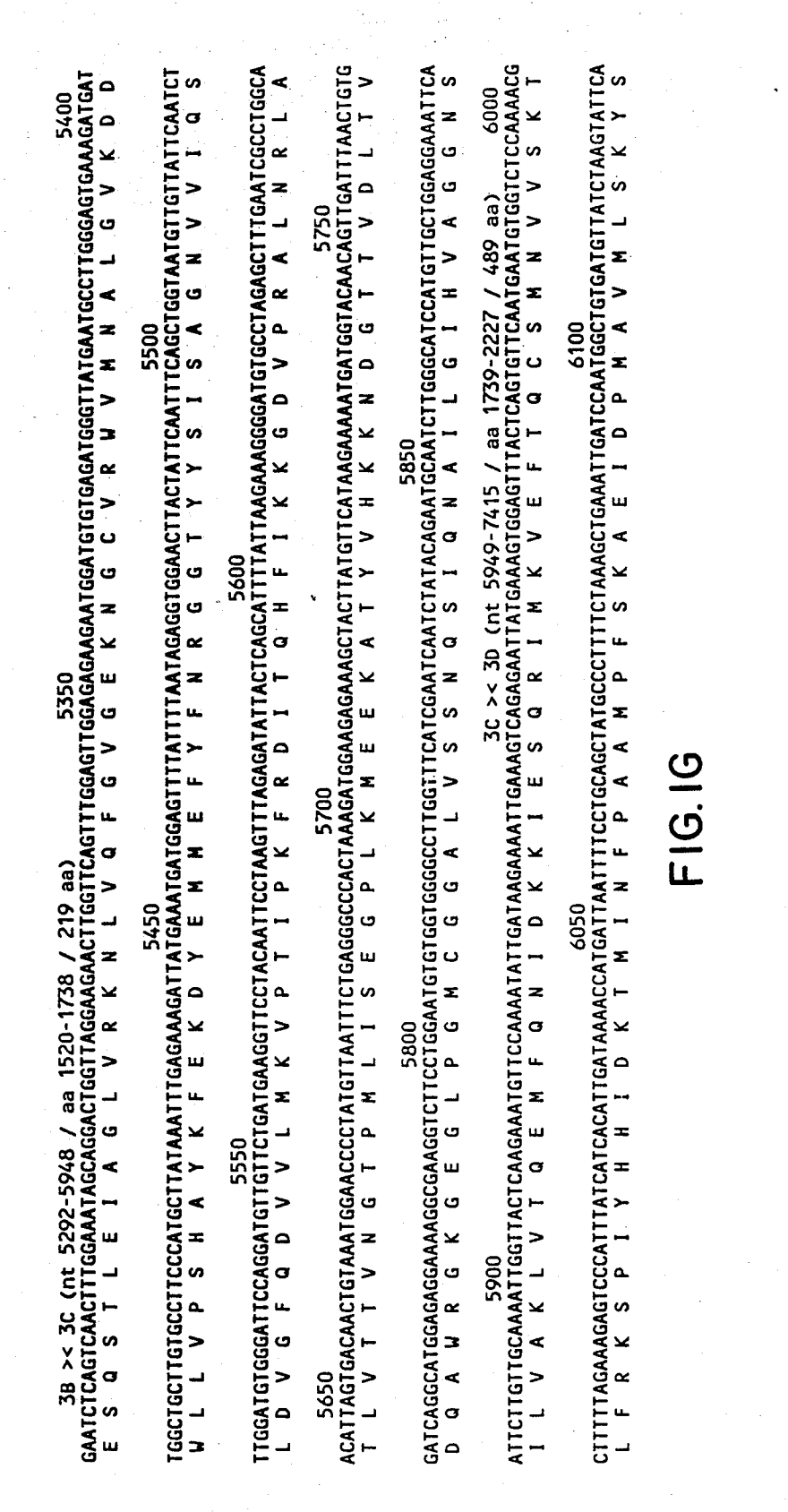

FIG. 1 shows the complete nucleotide sequence of wild-type hepatitis A virus, strain HM-175/7. Table 1 shows the differences between the nucleotide sequences of wild-type HAV HM-175 and attenuated HAV strain HM-175/7. Comparison of the two sequences shows 25 nucleotide changes distributed throughout the genome.

FIG. 2 shows ligation of cDNA clones to produce full-length wild-type HAV Hm-175 cDNA. Restriction endonuclease BstXI was used to ligate pHAV$_{LB}$228 (at base 3931 to pHAV$_{LB}$148 (at base 3970). The resulting plasmid, pHAV L1, has a 39 base deletion (bases 3931–3970). pHAV L1 was ligated to pHAV$_{LB}$24 at their common ApaI site (base 5687). The resulting plasmid, pHAV L2, was ligated to pHAV$_L$1307 at the NcoI site (base 2814) to produce pHAV L3. pHAV$_L$1688 was ligated to pHAV L3 at the XbaI site (base 744). The resulting plasmid, pHAV L4, was ligated to pHAV$_{Lr}$5375 at the common NcoI site (base 45) to yield pHAV L5. The deletion in pHAV L5 (bases 3931–3970) was repaired by a three-fragment ligation of restriction endonuclease fragments from pHAV L5 (SacI [base 2989]-EcoRI [base 4977]), pHAV$_{LB}$288 (SacI-HincII ]base 4242]), and pHAV$_{LB}$148 (HincII-EcoRI). The resulting plasmid, pHAV/WT BR322, contains full-length wild-type HAV HM-175 cDNA in plasmid pBR322. Partial restriction endonuclease digests were performed for plasmids pHAV$_{LB}$148 (BstXI), pHAV$_{LB}$24 (ApaI) and pHAV L4 (NcoI). Numbers refer to nucleotide positions in wild-type HAV HM-175 cDNA.

Figure 3:
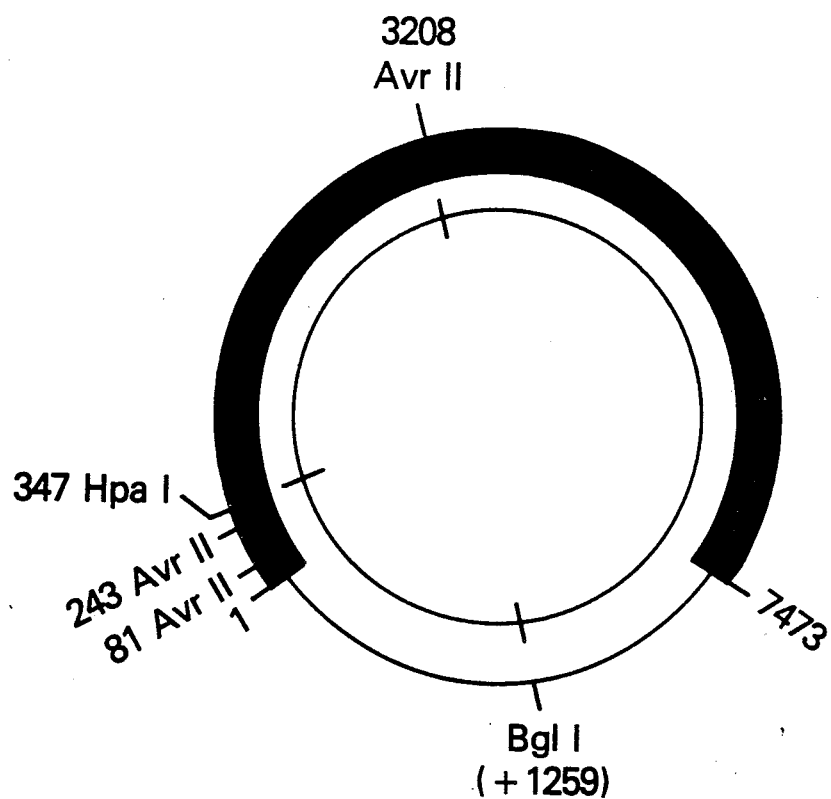

FIG. 3 shows the restriction endonuclease sites common to wild-type and attenuated HAV cDNA used to produce chimeric cDNAs. The solid bar indicates HAV cDNA, and the single line indicates pGEM1 DNA. The inner circle indicates restriction fragments used for ligations. Numbers refer to nucleotide positions in attenuated HAV HM-175 cDNA, number in parentheses refers to nucleotide position in PGEM1. AvrII cuts HAV cDNA at three positions; however, only the AVrII site at base 3208 was used to produce restriction fragments.

Figure 4:
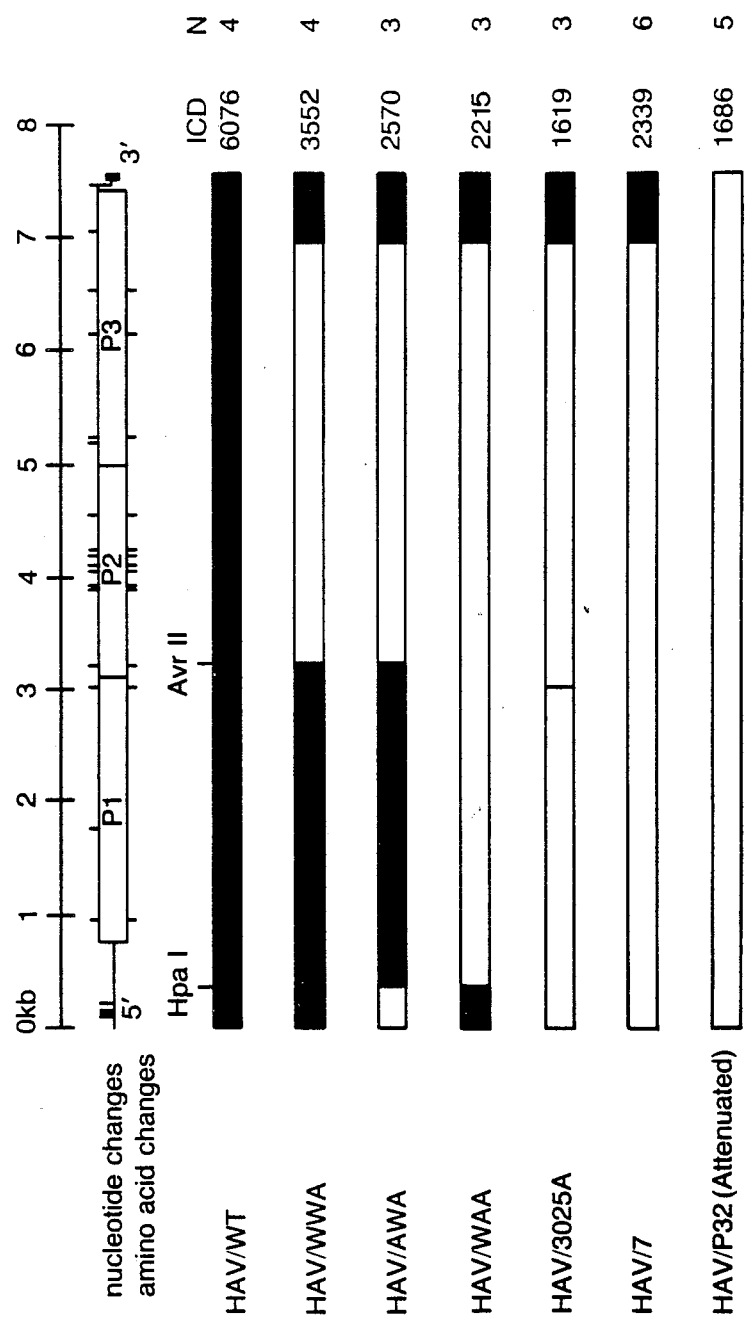

FIG. 4 shows the Genome structure of chimeric HAV cDNAs. The top line shows the length of the HAV genome in kilobases (kb) from the 5' terminus. The second line depicts the genome organization of HAV and the putative gene assignments with nucleotide (and amino acid) differences between wild-type and attenuated HAV HM-175 above (and below) the genome. The genome organization of infectious chimeric viruses is shown with attenuated HAV sequences (open bars) and wild-type sequences (closed bars) along with the restriction endonuclease sites used to divide the cDNAs. HpaI cuts attenuated HAV cDNA at base 347; all of the nucleotide changes between wild-type and attenuated HAV in the 5' noncoding region are 5' to this site. AvrII cuts attenuated HAV cDNA at base 3208; all of the nucleotide changes in the capsid region and one of the nucleotide changes in the gene encoding protein 2A are between the HpaI-AvrII sites. The region of the HAV genome 3' to AvrII contains the nucleotide changes in the P2 and P3 regions. Two of the nucleotide changes from wild-type HAV; bases 7027 and 7425, are not present in any of the chimeric cDNAs. The full-length attenuated HAV genome used to construct the chimeras does not contain these latter two base changes; hence, all of the constructs have wild-type bases at these two positions. ICD indicates geometric mean peak isocitrate dehydrogenase and N indicates number of marmosets inoculated.

Seven nucleotide changes occur in the 5' noncoding region, including 5 base deletions. At nucleotide position 203 to 207, a single thymine (out of 5 consecutive thymines in wild-type HAV) has been deleted in HM-175/7. Seventeen nucleotide changes occur in the amino acid coding region of the genome. Twelve of these base changes result in different amino acids, and seven of these yield amino acids of different charges. Four nucleotide changes occur in the capsid region. The changes in nucleotides 1742 and 2864 do not result in changes in the amino acids. The change in nucleotide 3025 yields a change in the amino acid sequence of VP1 from glutamic acid in wild-type HM-175 to valine in HM-175/7. This is the only amino acid change in the capsid region which results in an amino acid of different charge. One nucleotide change occurs in the 3' noncoding region—an additional thymine at the 3' end of the genome.

Ten amino acid changes between wild-type HAV HM-175 and HM-175/7 occur in proteins 2A, 2B, 2C, 3B and 3D. None of the amino acid changes occur at putative dipeptide cleavage sites or at proposed enzymatic sites of HAV proteins. The nucleotide difference at 6522 changes a serine in protein 3D of wild-type HAV HM-175 to a threonine in HM-175 Pass 35.

Wild type hepatitis A virus (HAV), strain HM-175 was originally recovered from the stool of a patient with hepatitis A and isolated in primary African green monkey kidney (AGMK) cells as is described in Daemer et al., *Infect. Immun.*, 32: 388–393 (1981). The virus was then passaged (up to 26 times) in AGMK cells and then triply cloned by the terminal dilution method. Some of these strains are available from the Americn Type Culture Collection under ATCC designation numbers VR 2089, VR 2090, VR 2091, VR 2092, VR 2093, VR 2097, VR 2098, and VR 2099. The triply cloned variant was then passaged three times in AGMK cells in order to prepare a stock of virus for primate inoculation. This later virus is attenuated for chimpanzees and elicits serum neutralizing antibody. This virus was then passaged three additional times in AGMK cells in order to produce the hepatitis A virus required to perform the cloning and sequence analysis of the present invention, HM-175/7. The entire nucleotide sequence of the genome of this virus is shown in FIG. 1.

Virus purification and RNA extraction. HAV is purified using a procedure described in Linemeyer et al, *J. Virology*, 54: 247–255 (1985). Briefly, AGMK cells infected with HAV are trypsinized, pelleted, resuspended in lysis buffer, sonicated twice for three minutes, and incubated on ice for 10 minutes. The sonicated debris is centrifuged at 10,000×g for 20 minutes, the resultant supernatant is centrifuged at 10,000×g for 20 minutes, and the resultant supernatant (from the second centrifugation) is removed and combined with sodium-Sarkosyl (SLS) to 0.5%. The supernatant from the first centrifugation, and pellets from the second and third centrifugation are pooled, resuspended in lysis buffer, and sonicated as above. The sonicated debris is centrifuged twice, as described above, and SLS is added to 0.5%. Both SLS supernatants are pooled, incubated at 37° C. for 30 minutes, and pelleted through a 40% sucrose cushion in lysis buffer for 20 hours at 100,000×g. The pellet is resuspended in 0.5% SLS in TNE, sonicated, and banded in 34% cesium chloride for 60 hours at 100,000×g. Fractions are collected assayed for refractive index, and tested for HAV by radioimmunoassay. The viral peaks are pooled, diluted 40-fold in 0.5% SLS in TNE, and pelleted at 100,000×g overnight. The pellet is resuspended in TNE and HAV RNA is extracted using known techniques. Molecular Cloning. HAV RNA (1.2 µg), obtained as described above, serves as a template for first-strand cDMA synthesis using well known techniques [described, for example, in Ticehurst et al, PNAS USA, 80: 5885–5889 (1983)]. In the preferred embodiment, the concentration of reverse transcriptase is increased to 1,000 U/ml and the reaction is incubated for 45 minutes. The reaction is terminated, RNA-cDNA hybrids are isolated, and second strand cDNA is synthesized using RNase H, *E. coli* DNA polymerase I, and *E. coli* DNA ligase. The reaction is terminated and double-stranded (ds) cDNA is isolated. ds cDNA is size selected using a 1 ml Sepharose 4B column. The first four 65 µl fractions containing ds cDNA are pooled and precipitated in ethanol after the addition of tRNA. Homopolymeric tails of cCMP are added to the ds cDNA using terminal deoxynucleotidyltransferase. The reaction is terminated, phenol extracted, and ethanol precipitated. Plasmid vector pBR322, cleaved at the Pst I site and tailed with dGMP, is hybridized to equimolar amounts of tailed ds cDNA and used to transform *E. coli* HB101, using standard procedures.

RNA transcripts of hepatitis A virus (HAV) HM-175 cDNA from an attenuated, cell culture-adapted HAV are infectious in cell culture. Cohen et al., *J. Virol.* 61: 3035–3039. A full-length HAV cDNA from wild-type HAV (propagated in marmosets in vivo) was constructed. Chimeric cDNAs were produced containing portions of both wild-type and attenuated genomes. Oligonucleotide-directed mutagenesis was used to engineer a point mutation into the VP1 gene of attenuated HAV cDNA, so that the sequence of this capsid protein would be identical to that of wild-type virus. Transfection of monkey kidney cells with RNA transcripts from several of the chimeric cDNAs and from the mutagenized cDNA induced production of HAV. Comparison of the growth of attenuated, wild-type, chimeric, and mutant viruses in vitro indicates that the P2–P3 (nonstructural protein) region may be important for cell culture-adaptation of the virus. Inoculation of marmosets with transfection-derived virus also suggests that the P2–P3 region may play an important role in attenuation of HAV HM-175. See FIGS. 2, 3, 4 and Tables 2 and 3. Site directed mutagenesis was also used to individually back mutate the other mutations found in the attenuated pass 35 strain of HM-175 to the sequence of the wild-type. These mutations were tested for their ability to grow in cell culture. When the cytosine at position 3919 and the thymine at position 3889 were back mutated to guanine and cytosine respectively, the virus lost its ability to grow in cell culture.

The vaccine developed from the present invention is suitable for use in mammals or higher primates, including man, chimpanzees, and marmosets. Either triply cloned or twice cloned viral material may be used in the present invention, however, triply cloned viral material is homogeneously superior to the twice cloned virus material for a uniform virus preparation suitable for a vaccine.

In the preferred embodiment, master seed lots of HAV HM-175 are triply cloned by terminal dilution at passage levels 10, 20 and 30 [Cunningham, *A Laboratory Guide in Virology*, 5th edition, Burgess Publishing Company, pp. 144–145 (1963)]. The purpose of the dilution is that the highest dilution positive tubes of the procedure originate from a single virus particle, thus providing biological uniformity of the product.

While the strain of the present invention may be produced by cell culture, other methods may be used, for example, in vitro mutagenesis and transfection by cDNA. Furthermore, although the preferred method is propagation in cell culture, the viral genome may be amplified by use of a prokaryotic or eukaryotic vector, or in vivo.

EXAMPLE

In order to analyze the cDNA clones and determine the nucleotide sequence of the HAV genome of the present invention, bacterial clones obtained as described in the Specific Disclosure were transferred to nitrocellulose filters, lysed, and the DNA was bound. Three HAV cDNA probes were prepared corresponding to the middle, 5', and 3' ends of wild-type HAV-cDNA. DNA fragments from plasmids $pHAV_{LB}113$ (Nco I/Xba I digest), $pHAV_{LB}228$ (Pst I digest), and $pHAV_{LB}93$ (Pst I digest) were isolated from agarose gels, nick-translated, and used as probes for hybridization. Approximately 5,000 bacterial clones were screened by colony hybridization to the radiolabeled HAV cDNA clones. The nucleotide sequence of the HAV genome of the present invention was determined directly from plasmid DNA using reverse transcriptase, oligonucleotide primers, and dideoxynucleotide triphosphates, using standard techniques.

It is understood that the examples and embodiments described herein are for illustrative purposes only and that various modifications or changes in light thereof will be suggested to persons skilled in the art and are to be included within the spirit and purview of this application and scope of the appended claims.

TABLE 2

In vitro and in vivo transfections with HAV cDNA and its RNA transcripts

| Transfection of Secondary AGMK Cells | HAV Produced |
| --- | --- |
| pHAV/7 RNA | + |
| pHAV/7 DNA | + |
| pHAV/3025A RNA | + |
| pHAV/WAA RNA | + |
| pHAV/WWA RNA | + |
| pHAV/AWA RNA | + |
| pHAV/AAW RNA | – |
| pHAV/AWW RNA | – |
| pHAV/WAW RNA | – |
| pHAV/WT RNA | – |
| pHAV/WT DNA | – |
| Intrahepatic Inoculation of Marmosets | HAV Seroconversion |
| pHAV/7 RNA | – |
| pHAV/7 DNA | – |
| pHAV/AAW, pHAV/AWW, pHAV/WAW pooled RNA | – |
| pHAV/WT RNA | – |
| pHAV/WT DNA | – |

TABLE 1

| Nucleotide | Base | | Amino Acid | | | | Base | | |
| --- | --- | --- | --- | --- | --- | --- | --- | --- | --- |
| Position | WT | HM-175/7 | WT | HM-175/7 | LA | CR-326 | HM pass 59 | HAS-15 | Italy |
| 124 | T | C(C,C) | | | T | — | T | — | T |
| 131 | T | d(d,d) | | | T | — | T | — | C |
| 132 | T | d(d,d) | | | T | — | T | — | T |
| 133 | T | d(d,d) | | | T | — | T | — | T |
| 134 | G | d(d,d) | | | G | — | G | — | G |
| 152 | A | G(G,G) | | | A | — | A | — | A |
| 203–207 | T | d(d,d) | | | A | — | d | — | — |
| 964 | A | G(G) | Lys | Arg | A | A | A | A | — |
| 1742 | G | A | | | T | C | — | T | — |
| 2864 | T | A(A) | | | G | A | — | A | — |
| 3025 | A | T(T) | Glu | Val | A | A | — | A | — |
| 3196 | A | G(G,G) | Asn | Ser | A | A | — | A | — |
| 3889 | C | T(T,T) | Alu | Val | C | — | — | C | — |
| 3919 | G | C(C,C) | Gly | Ala | G | — | — | G | — |
| 4043 | T | C(C,C) | | | T | — | — | T | — |
| 4087 | A | T(T,T) | Lys | Met | A | — | — | A | — |
| 4185 | G | A(A) | Glu | Lys | A(Asn) | — | — | A(Asn) | — |
| 4222 | T | C(C) | Phe | Ser | T | — | — | T | — |
| 4563 | G | A(A) | Val | Ile | G | — | — | — | — |
| 4810 | T | C(T,T) | Phe | Ser | T | — | — | — | — |
| 5204 | G | A(A) | | | A | — | — | — | — |
| 5232 | C | T(T) | His | Tyr | C | — | — | — | — |
| 6147 | G | A(A,A) | Asp | Asn | G | — | — | — | — |
| 6522 | T | A(A,A) | Ser | Thr | A(Thr) | — | — | — | — |
| 7032 | T | C(C,C) | | | T | — | — | — | — |
| 7430 | A | G(G,G) | | | A | — | — | — | — |
| 7433 | T | C(T,T) | | | T | — | — | — | — |
| 7479 | A | T(A,A) | | | A | — | — | — | — |

WT = wild-type HM-175
LA = Najarian et al (PNAS 1985)
CR-326 = Linemeyer et al (JV 1985)
pass 59 = Ross (JGV 1986)
HAS-15 = Ovchinnikov et al (DANS 1986)
Italy = Venuti et al (JV 1985)

Nucleotide positions correspond to numbering for wild-type HM-175 (Cohen 1986). Bases in parentheses indicate bases sequenced on additional clones, hyphens indicate nucleotide sequences not determined, amino acids in parentheses indicate amino acid differing from wild-type HM-175. Nucleotide 4810 is a thymine in wild-type HAV HM-175 and two of the three cDNA clones from HM-175/7.

Nucleotide 7433 is T in wild-type HAV HM-175 and two of three cDNA clones from HM-175 Pass 35; the third cDNA clone has a C at base 7433. An additional T is added at the 3' end of the genome in one of three cDNA clones of HM-175 Pass 35. The nucleotide sequences of the cell culture adapted strains (e.g., LA, Cr-326, etc.) differ from wild-type HM-175 in more positions than indicated here; nucleotides listed are only those where wild-type HM-175 differs from HM-175/7.

Citations:

Najarian et al, PNAS, 79:5793–5797 (1982).
Linemeyer et al, J. Virol., 54:247–255 (1985).
Ross et al, J. Gen. Virol., in press.
Ovchimmikov et al, Dokl Akad Nauk SSSR, 285:1014–1018 (1985).
Cohen et al, "Nucleotide sequence of wild-type hepatitis A virus," in press.

TABLE 3

Liver enzymes of marmosets receiving transfection-derived viruses

| Inoculum | Marmoset number | Peak ICD level (sigma units/ml) | Week After Inoculation Until Peak ICD level | Week After Inoculation Until Positive anti-HAV antibody |
|---|---|---|---|---|
| HAV/7 | 460 | 3,230 | 9 | 8 |
|  | 517 | 2,023 | 10 | 10 |
| HAV/3025A | 501 | 1,419 | 8 | 6 |
|  | 506 | 1,315 | 2 | 5 |
|  | 534 | 2,276 | 12 | 8 |
| HAV/WAA | 532* | 1,523 | 11 | 11 |
|  | 552 | 2,430 | 5 | 3 |
|  | 485 | 2,930 | 8 | 6 |
| HAV/AWA | 479 | 8,147 | 7 | 7 |
|  | 489 | 1,676 | 7 | 7 |
|  | 522 | 1,245 | 9 | 7 |
| HAV/WWA | 525 | 3,265 | 5 | 5 |
|  | 526 | 3,173 | 8 | 5 |
|  | 528 | 5,298 | 5 | 4 |
|  | 529 | 2,904 | 7 | 5 |

*Serum for ICD determination was not obtained four weeks prior to seroconverion for this animal.

What is claimed is:

1. An attenuated hepatitis A virus comprising a genome characterized by the following nucleotides: cytosine at positions 3919, 4043, 4222 and 4810; guanine at positions 964 and 3196; adenine at positions 1742, 2864, 4185, 4563, 5204, 6147 and 6522; and thymine at positions 3025, 3889, 4087 and 5232.

2. The attenuated hepatitis A virus of claim 1 wherein said genome encodes the following amino acids: an arginine is encoded at nucleotide position 964; valine at nucleotide positions 3196, 4222 and 4810; alanine at position 3919; methionine at position 4087; lysine at position 4185; isoleucine at position 4563; tyrosine at position 5232; asparagine at position 6147; and threonine at position 6522.

3. A tissue culture adapted hepatitis A virus comprising a genome characterized by a cytosine at nucleotide position 3919 and a thymine at nucleotide position 3889.

4. The tissue culture adapted hepatitis A virus of claim 3 wherein said genome encodes the following amino acids: an alanine at nucleotide position 3919 and a valine at nucleotide position 3889.

5. A pharmaceutical composition, comprising immunogenic amount of the virus of claim 4 and pharmaceutically acceptable carrier.

6. A method for inducing protective immunity against HAV, comprising administering to a host susceptible to HAV infection, immunogenic amount of hepatitis A virus comprising a genome coding for alanine at nucleotide position 3919 and valine at nucleotide position 3889, to render said host immune to HAV infection.

* * * * *